United States Patent [19]

Carson

[11] Patent Number: 4,692,460
[45] Date of Patent: Sep. 8, 1987

[54] CYCLOPENTA[B]THIOPHENES HAVING ANTI-INFLAMMATORY ACTIVITY SIMILAR TO STEROIDS

[75] Inventor: John R. Carson, Norristown, Pa.

[73] Assignee: McNeilab, Inc., Fort Washington, Pa.

[21] Appl. No.: 946,555

[22] Filed: Dec. 24, 1986

[51] Int. Cl.$^4$ .................... A61K 31/38; C07D 333/56
[52] U.S. Cl. ........................................ 514/443; 549/57
[58] Field of Search .......................... 549/57; 514/443

[56] References Cited

U.S. PATENT DOCUMENTS 3,647,858  3/1972  Hinkley et al. ...................... 260/470

FOREIGN PATENT DOCUMENTS

A4362585  1/1986  Australia .

OTHER PUBLICATIONS

Chem Abst 1981, 95:42895n, Adroher et al.

Primary Examiner—Alan Siegel
Attorney, Agent, or Firm—David J. Levy

[57] ABSTRACT

Cyclopenta[b]thiophenes of the following formulae (I) and (II):

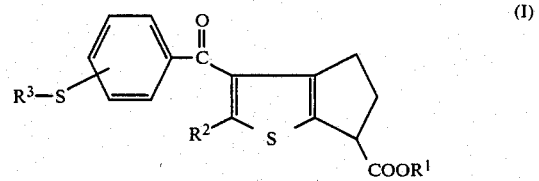

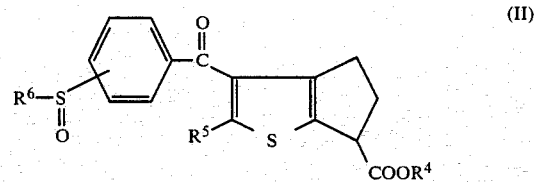

wherein
$R^1$ and $R^4$ are H or alkyl and $R^2$, $R^3$, $R^5$ and $R^6$ are alkyl, as well their salts, are anti-inflammatory agents having pharmacological profiles similar to that of steroids. Also part of the invention are pharmaceutical compositions and methods for the pharmaceutical treatment of mammals such as man.

15 Claims, No Drawings

CYCLOPENTA[B]THIOPHENES HAVING ANTI-INFLAMMATORY ACTIVITY SIMILAR TO STEROIDS

Inflammation is a response of mammals to a variety of stimuli including trauma and exposure to temperature extremes as well as disturbances of the immune system resulting in diseases such as rheumatoid arthritis. Modification of the inflammatory response in the treatment of various diseases often relies upon agents chosen from one or both of the two main classes of effective drugs the steroidal and non-steroidal (NSAID) anti-inflammatory drugs. The two classes may sometimes give the same result, but since they operate by entirely different mechanisms, it is often found that a drug from one class will be effective while one from the other will not. For example, inflammation caused by poison ivy will be refractory to an NSAID such as aspirin and yet responsive to a steroid such as hydrocortisone. In addition, both classes have typical side effects which are distinct from each other. Thus, an extended steroid regimen may involve the appearance of cataracts, glaucoma and osteoporosis. NSAIDs can be tolerated for longer periods of time and while less toxic as a class, also have significant side effects including headaches, diarrhea and other gastrointestinal problems. It can be seen from the literature that agents from the two classes have significantly different pharmacological profiles and actions. Publications include A. Viaje et al. in Cancer Research, 37, 1530–1536 (1977) and R. P. Carlson in Agents and Actions, 17, 2, 197–204.

It is an object of the present invention to provide a class of anti-inflammatory agents which have a non-steroidal chemical structure and yet which act in established pharmacological tests like steroidal anti-inflammatory agents. Thus, the agent would in this respect be similar to sulindac as described in U.S. Pat. No. 3,654,349 and 3,647,858.

SUMMARY OF THE INVENTION

Alkyl sulfide and sulfoxide derivatives of cyclopenta[b]thiophene of the following formulae (I) and (II):

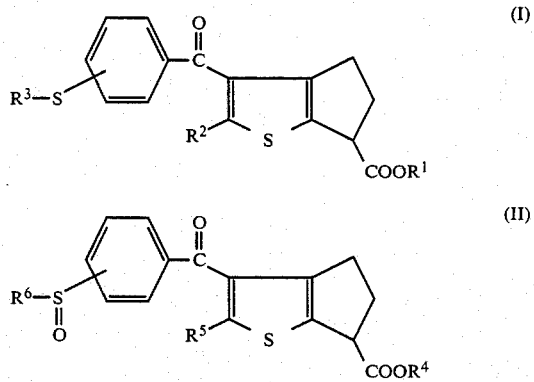

wherein
$R^1$ and $R^4$ are hydrogen or alkyl and $R^2$, $R^3$, $R^5$ and $R^6$ are alkyl and salts thereof have been found to be active in pharmacological tests which usually only show activity for the steroidal anti-inflammatory drugs and specially not the cyclooxygenase inhibitors. The invention compounds may be used as anti-inflammatory agents or in suppressing the immune response to transplants.

DETAILED DESCRIPTION OF THE INVENTION

The invention compounds comprise those of the following formula (I) and (II):

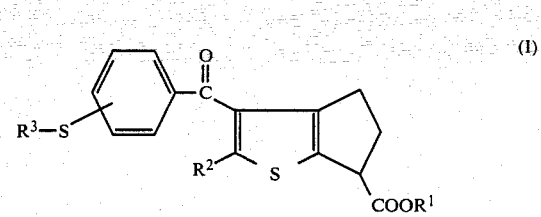

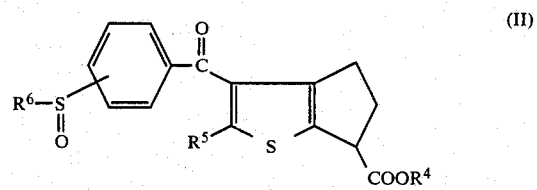

wherein
$R^1$ and $R^4$ are hydrogen or alkyl;
$R^2$ and $R^5$ are alkyl; and
$R^3$ and $R^6$ are alkyl and the pharmaceutically acceptable base-addition salts thereof when $R^1$ or $R^4$ is hydrogen.

In particular, alkyl for $R^1$–$R^6$ includes straight and branched chain alkyl of about 1 to 6 carbons. The $R^3S$— and $R^6SO$—moieties may be at the ortho, meta or para positions. Specific examples include compounds wherein $R^1$ and $R^4$ are hydrogen, $R^2$, $R^3$, $R^5$ and $R^6$ are methyl and the sulfide and sulfoxide moieties are at the para position. For example, compounds include:

5,6-Dihydro-2-methyl-3-[4-(methylthio)benzoyl]-4H-cyclopenta[b]thiophene-6-carboxylic acid; and
5,6-Dihydro-2-methyl-3-[4-(methylsulfinyl) benzoyl]-4H-cyclopenta[b]thiophene-6-carboxylic acid Base addition salts for use in the invention of formula (I) when $R^1$ is hydrogen and of formula (II) when $R^4$ is hydrogen include those formed with an alkali metal or alkaline earth metal hydroxide, $NH_4OH$, an organic amine such as triethylamine, morpholine or cyclohexylamine, tert-butylamine or tromethamine.

Compounds of formulae (I) and (II) and other compounds of the invention may exist in various isomeric forms, e.g., in view of the presence of an asymmetric carbon, in particular at position 6 of the ring system although other asymmetry may exist, e.g. when an alkyl group is sec-butyl. It is understood that the present invention includes all such individual isomers and their racemates. Also within the scope of the invention are compounds of the invention in the hydrates and other solvate forms as well as polymorphic crystalline forms.

Compounds of formula (I) and (II) may be prepared by reaction sequences summarized in the reaction scheme and exemplified in the following examples. In the formulae of the Reaction Scheme, $R^2$ is as described for formula (I).

A 5-alkyl-2-thiophenecarboxaldehyde of formula (III) such as 5-methyl-2-thiophenecarboxaldehyde, is condensed with diethyl malonate under Knoevenagel conditions, e.g. in the presence of piperidine and benzoic acid at elevated temperatures of about 50° to 100° C. The solvent used is one capable of azeotropic removal of water, e.g. benzene or toluene and the product obtained is the unsaturated diester (IV).

Treatment of the unsaturated diester (IV) with diethylaluminum cyanide under an inert atmosphere and preferably at a reduced temperature of 15 to $-78°$ C. in an inert aprotic solvent such as toluene, THF or hexane yields the saturated diester (V).

The unsaturated diester (V) may be heated in DMSO at about 50–189° C. with or without an added salt such as NaCl or NaCN and traces of water to yield the monoester (VI). Alternatively, treatment of the unsaturated diester (IV) with KCN in a lower alcohol gives the monoester as in Modification A, which follows the examples.

Reaction Scheme

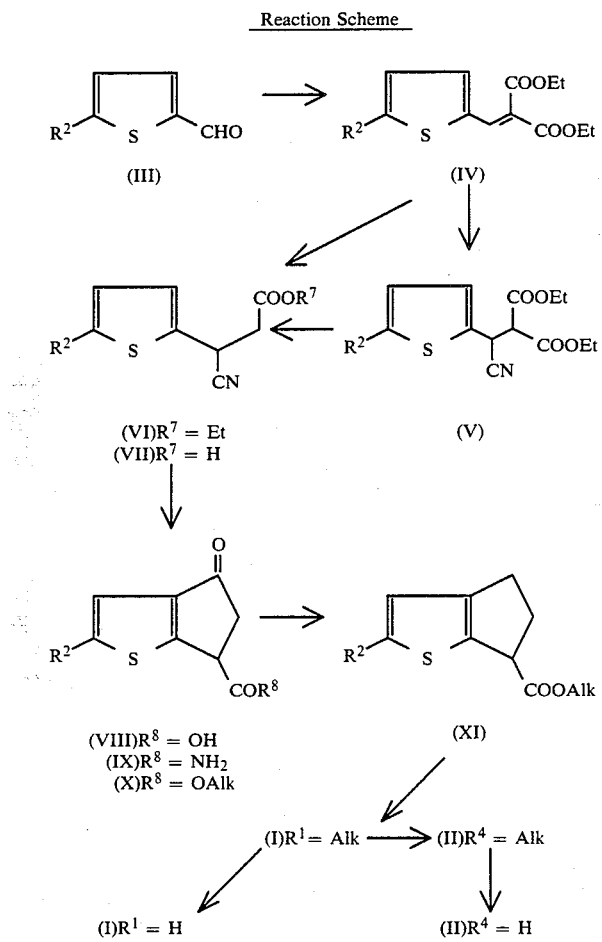

The monoester (VI) is then saponified with an alkali metal hydroxide at 25° to 80° C. in water or an alcoholic solution to yield the monoacid (VII). Treatment of the monoacid (VII) with polyphosphoric acid (PPA) at about 60° to 120° C. followed by addition of water and further heating at 50° to 100° C. affords ketoacid (VIII) with a strong acid such as HCl, $H_2SO_4$, $CH_3SO_3H$ or toluenesulfonic acid in an alcohol of the formula Alk-OH where Alk is straight or branched chain alkyl of about 1 to 6 carbons at a temperature of about 40 to 80° C. gives the ketoester (X). Alternatively, PPA cyclization without subsequent hydrolsis yields both the ketoacid (VIII) plus the ketoamide (IX) which can be combined and converted to the ketoester (X) by treatment with the strong acid and Alk-OH as shown below in Modification B.

The ketoester (X) may be reacted in a Clemmenson reduction with zinc and HCl, preferably at a reduced temperature of about $-15°$ to $+15°$ C. in an anhydrous ethereal solvent such as $Et_2O$ or THF to yield the ester (XI).

The ester (XI) may undergo a Friedel Crafts acylation with a benzoyl chloride of the formula $R^3$-S-phenyl-COCl, e.g. p-methylthiobenzoyl chloride, in the presence of a Lewis acid such as $SnCl_4$, $AlCl_3$ or $BF_3$ in an inert solvent such as $CH_3NO_2$, $ClCH_2CH_2Cl$, $CH_2Cl_2$, $CHCl_3$, nitrobenzene or $CS_2$ and at a temperature of about $-78°$ C. to $+100°$ C. to yield (I) where $R^1$ is Alk. Saponification of the product with an inorganic base such as NaOH, KOH, $BaaOH)_2$, $K_2CO_3$ or LiOH or a quaternary ammonium hydroxide preferably in water or with a water miscible organic co-solvent such as a lower alkanol or dioxane at about 0° to 120° C. yields sulfide (I) where $R^1$ is H. Alternatively, the hydrolysis may be carried out by heating with an aqueous strong acid such as HCl, $H_3PO_4$ or $H_2SO_4$.

Oxidation of sulfide (I) where $R^1$ is alkyl with hydrogen peroxide, periodate or an organic peracid yields the sulfoxide (II) where $R^4$ is alkyl. The oxidation with hydrogen peroxide is preferably carried out in acetic acid or acetone at about room temperature to yield the sulfoxide (II). Hydrolysis of the sulfoxide (II) where $R^4$ is alkyl to yield the acid where $R^4$ is H is carried out as described for the saponification of sulfide (I) where $R^1$ is alkyl to yield (I) where $R^1$ is H.

The anti-inflammatory activity of the compounds of the present invention may be evaluated by the Phorbal Induced Inflammation Test as described below.

Phorbal Induced Inflammation Test

The phorbol ester 12-O-tetradecanoylphorbol-13-acetate (TPA) is one of a series of plant diterpenes which have been widely studied as tumor promoters. Repeated administration of these agents can enhance the response of a target organ to a suboptimal dose of carcinogen to yield full expression of tumorigenesis. TPA alone is not carcinogenic. The target organ most frequently studied is mouse skin. In mouse skin, the acute topical administration of TPA has been shown to produce a severe inflammatory event characterized by edema and cellular infiltration followed by epidermal hyperplasia (Raick, A. N. in Cancer Res. 33, 269–286, 1973). The phorbol ester-induced inflammation and subsequent tumor promotion are poorly controlled by non-steroidal anti-inflammatory drugs but can be suppressed by steroids (Fischer, S. M., et al. in Cancer Lett. 10, 343–350, 1980 and Viaje, A., et al. in Cancer Res. 37, 1530–1536, 1977). The response of mouse epidermis has been variously interpreted as a model for psoriasis, acute allergic dermatitis, and carcinogenesis. The following protocol describes the use of the model to study orally active anti-inflammatory agents with steroidal-like activity. Myeloperoxidase activity was used as a marker of neutrophil infiltration. The levels of serum proteins in edema fluids was used as an indicator of protein extravastion in the inflamed tissue and was used to quantify edema. Hence, two components of phorbol ester induced inflammation, edema and cellular infiltration were examined. The known non-steroidal anti-inflammatory drugs suppress edema but not myeloperoxidase accumulation. Steroids and colchicine suppress both components.

The dorsal skin of mice was shaved at least 16 hrs prior to experiments. Test agents were administered by oral gavage in 0.5% methyl cellulose vehicle. A volume of 100 μL per 10 gm of body weight was administered, and vehicle treated controls were run for each experiment. Immediately after administration of the test compound, 25 μg of the phorbol ester TPA was applied in a 25 μL volume of acetone containing red ink to mark the treated skin area. The inflammation of the skin was allowed to develop for the next 7 hrs. Then the animals were sacrificed by $CO_2$ asphyxiation. The inflamed dorsal skin was removed and an 8 mm diameter skin punch was prepared using a stainless steel skin biopsy punch (Roboz Surgical Equipment, Washington, D.C.). The skin samples were immediately placed in 1.0 mL ice cold phosphate buffered saline (PBS) and centrifuged at 12,000×g for 10 min to extrude the edema fluids from the skin. The PBS plus edema fluid supernatants were immediately quick-frozen on dry ice and stored at −70° C. until assayed for total protein content. The remaining skin punch samples were placed in 1.0 ml of homogenization buffer consisting of 0.5% hexadecyltrimethylammonium bromide in 50 mM sodium phosphate buffer at pH 5.4 as described by Williams et al. in Current Eye Research 2, 465-470, (1982/1983). The samples were frozen on dry ice and stored at −70° C. until assays for myeloperoxidase were performed.

Myeloperoxidase is an enzyme marker for neutrophils. The appearance of myeloperoxidase activity in homogenates of inflamed skin has been previously shown to correlate with the degree of cellular infiltration at a site of inflammation (Bradley, P. P., et al. in J. Inves. Dermatol. 78, 206-209, 1982). Myeloperoxidase activity was measured using the procedure of Suzuki et al. in Anal. Biochem. 132, 345-352, (1983). After thawing at 37° C., the skin samples were homogenized in an Ultraturrax tissue homogenizer and then sonicated for 2 sec with a Biosonic sonicator fitted with a microprobe. The homogenates were centrifuged at 12,000×g for 20 min. Supernatant (70 μL) was added to 750 μL of 50 mM sodium phosphate buffer at pH 5.4 followed by 30 82 1 of 3,3',5,5'-tetramethylbenzidine (TMB) dissolved in dimethylformamide. The final TMB concentration was 1.6 mM. The myeloperoxidase reaction was initiated by the addition of 150 μL of a 0.03% $H_2O_2$ solution in 50 mM sodium phosphate buffer. The reactions were incubated at 37° C. for 2 min in a shaking water bath. The reactions were placed on ice and terminated by adding 2 ml of 200 mM sodium phosphate, pH 3.0. Myeloperoxidase activity was determined as the absorbance of the blue colored reaction product at a wavelength of 595 nm in a Beckman DU8B spectrophotometer.

Levels of edema proteins measured in the PBS/edema exudate samples by the method of Lowry et al. in J. Biol. Chem. 193, 265-275 (1951). The tetravasation of plasma proteins are responsible for the rise in proteins observed in exudate fluids during inflammation.

Absorbence values and protein determinations were normalized to vehicle treated control values and expressed as percent inhibition. Values for percent inhibition were plotted against the log dose of compound. Linear regression analysis was performed on these data to estimate the dose of test agent which produced a 50% suppression of either the appearance of myeloperoxidase ("Myeloperoxidase Accumulation") or edema protein accumulation ("Edema").

A second pharmacological test used to evaluate the activity of the compounds of the present invention against arthritis is the Graft versus Host Reaction (GVHR). The following review is offered in order to explain the relevance of the GVHR to arthritis.

It is well accepted that immune dysfunction plays a major role in rheumatoid arthritis and this is the basis for the use and continued investigation of immunomodulatory drugs to treat this progressive degenerative disease. Although the etiologic agent has to be identified, it is quite clear that an abnormal and in some way, self-perpetuating, immune response is involved in the maintenance of this chronic inflammatory disease. It has been suggested that the distinction between those who develop arthritis and those who do not may be more closely associated with variability in immune response than with exposure to any individual infectious agent. Individual variations in the capacity to mount an immune response to a particular antigen can be traced to genes that encode products of the major histocompatibility complex (MHC), and there are suggestions that there is a relationship between the propensity to develop arthritis and the inheritance of the HLA-DR4 genotype. In one study, 70% of patients with rheumatoid arthritis were demonstrated to possess the HLA-D4 genotype whereas only 28% of controls were D4-positive.

There is good evidence of extensive immunological activity in the rheumatoid synovium, literature teachings include its resemblance to an activated lymph node and similarities between the histological characteristics of the inflamed synovium and a delayed hypersensitivity reaction. Certain experimental animal models of arthritis are strain specific and influenced by the MHC, and adjuvant arthritis in the rat can be controlled by specific, cloned T-cell lines. These and other observations strongly support a role for T-cells in the pathogenesis of rheumatoid arthritis and other connective tissue diseases.

The GVHR is a T-cell mediated, delayed hypersensitivity reaction in which donor lymphocytes recognize the histocompatibility antigens of the host, become activated, and initiate cell-mediated and humoral responses to host tissues. In a similar manner, rheumatoid arthritis involves an immune response to its own tissues, i.e., an autoimmune reaction with many of the characteristics of the GVHR. Furthermore, it has been demonstrated that the induction of a sustained GVHR will culminate in the development of a chronic progressive polyarthritis with many of the histological features of human rheumatoid arthritis.

GVHR Test

Parental donor Lewis and LeBNF1 strain rats (7-9 week-old females) were bled (5.0 ml) by cardiac puncture into 10.0 ml plastic syringes containing 0.08 ml aqueous (10%) EDTA. The anticoagulant-treated blood samples from each rat strain were pooled.

Lymphocytes were extracted in Lymphocyte Separation medium. Four volumes of rat blood (diluted 1:1 with sterile normal saline) were laid over three volumes of Lymphocyte Separation medium in 50 ml conical sterile plastic centrifuge tubes (with screw-cap). After centrifugation at 400×g for 40 min at 24° C., the lymphocytes which localize as a narrow band in the center of the gradient were harvested. The lymphocyte suspension was washed twice in the sterile normal saline and the suspension adjusted to $5.0 \times 10^7$ viable lymphocytes per ml in saline.

The regional GVHR was induced in five-week-old LeBNF1 hybrid rats by injecting $0.1 \times 10^7$ parental Lewis strain lymphocytes, in a 0.5 ml volume per hind foot pad. LeBNF1 hybrid lymphocytes at the same cell concentration were injected into LeBNF1 recipients to provide a syngeneic control.

On the seventh day following lymphocyte graft inoculation into LeBNF1 recipients, the rats were weighed, sacrificed in a $CO_2$ chamber and s single popliteal node surgically removed from each hind leg. Immediately after node excision, the node was wrapped in a prelabeled square of aluminum foil and stored at −70° C. until weighed. The nodes were weighed as frozen organs. The node weights in the data represent the geometric mean of the averages of paired nodes from each animal in a single LeBNF1 recipient group.

The GVHR intensity was measure by expressing the popliteal node weight/body weight indexes.

Popliteal Node Weight/Body Weight Index=A/B where APopliteal Node Weight:Body Weight ratio of the allogeneic control
where BPopliteal Node Weight:Body Weight ratio of syngeneic control The popliteal node weight/body weight index is reported in the Bio-Assay System as NBI.

Drug Effect: Immunosuppression of GVHR

Percentage of inhibition of the GVHR-induced node/body weight ratio was calculated by the following formula:

$$(100 - C) \times 100$$

where C. is the difference between the Node/Body Wt. Index (medicated) and the Node/Body Wt. Index (syngeneic) as divided by the difference between the Node/Body Wt. Index (sham) and the Node/Body Wt. Index (syngeneic).

Part of the present invention are pharmaceutical compositions containing an effective anti-inflammatory amount of a compound (including salts) of formula (I) or (II) in combination with a pharmaceutically acceptable carrier. An effective amount would be, in particular, about 0.5 to 100 mg per kg of body weight of the mammal being treated, administered orally or parenterally. To prepare the pharmaceutical compositions of this invention, one or more compounds or salt thereof of the invention as the active ingredient, is intimately admixed with a pharmaceutical carrier according to conventional pharmaceutical compounding techniques, which carrier may take a wide variety of forms depending on the form of preparation desired for administration, e.g., oral, topical or parenteral. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, patch capsule, powder, injection, teaspoonful and the like, from about 1 to 1000 mg of the active ingredient, and, preferably, from about 10 to about 60 mg.

In the following examples and throughout the specification, the following abbreviations may be used: mg (milligrams); g (grams); ml (milliliters); $\mu$l (microliters); L (liters); sec (seconds); hr (hours); min (minutes); mM (millimolar); M (molar); N (normal); mp (melting point); bp (boiling point); mm (millimeters); nm (nanometers); Et (ethyl); $Et_2O$ (diethyl ether); EtOAc (ethyl acetate); MeOH (methanol); EtOH (ethanol); PPA (polyphosphoric acid); THF (tetrahydrofuran); DMSO (dimethylsulfoxide); p.o. (per os, orally); i.p. (intraperitoneal); and C,H,N,O, etc. (the chemical symbols for the elements). Unless otherwise indicated, all temperatures are reported in °C. (degrees centigrade).

EXAMPLE 1 a. Diethyl 2-[5-Methyl-2-thienyl)methylene]propanedioate

A 215 g (1.71 moles) sample of 5-methyl-2-thiophenecarboxaldehyde, 258 ml (1.71 moles) diethyl malonate, 25 ml piperidine, 0.52 g benzoic acid, and 1.5 L toluene were placed into a round bottom flask and heated to reflux for four hr. with azeotropic removal of water. The reaction was cooled and water was added. The toluene layer was washed with sodium bicarbonate solution. 3N hydrochloric acid, water, brine and dried ($MgSO_4$). The solvent was evaporated in vacuo. The residue was washed with methylcyclohexane. The washings were collected, the solvent removed in vacuo and the residue was recrystallized from methylcyclohexane. The solid materials were combined to give 299.86 g of diethyl 2-[(5-methyl-2-thienyl)methylene]propanedioate, mp 53°–56° C.

b. Diethyl 2-[Cyano(5-methyl-2-thienyl)methyl]-propanedioate

A 50.60 g (0.189 moles) sample of diethyl 2-[(5-methyl-2-thienyl)methylene]propanedioate, the product of Example 1a., was taken up in 560 ml dry THF. The solution was cooled in an ice bath. 560 ml of 1N diethyl aluminum cyanide in toluene (0.57 moles) was added dropwise over one hr. The ice bath was then removed and the reaction was stirred at room temperature for 1.5 hr. After this time the reaction was cooled again in an ice bath and 168 ml of 3N sodium hydroxide was added slowly. This was stirred for one hr. The reaction was partitioned between methylene chloride and water, the organics were washed with water, brine, and dried ($MgSO_4$). The solvents were evaporated in vacuo. The residue was distilled in a Kugelrohr at 140° C. and 0.005 mm Hg. 117.17 g of diethyl 2-[cyano(5-methyl-2-thienyl)methyl]-propanedioate was collected as an oil.

c. Ethyl $\beta$-Cyano(5-methyl-2-thiophene)propaneoate

A 117.71 g (0.40 moles) sample of diethyl 2-[cyano (5-) methyl-2-thienyl)methyl]propanedioate, the product of Example 1b., was taken up in 360 ml DMSO and 14.12 ml water. 23.34 g (0.44 moles) sodium chloride was added and the reaction was heated to 145° C. for six hr. The heat was turned off and the reaction was stirred overnight at room temperature. The reaction was partitioned between Et$_2$O and water. The aqueous layer was extracted three times with Et$_2$O and the organics were combined, washed with water (two times), brine, and dried (MgSO$_4$). After removing the solvent in vacuo the residue was distilled in a Kugelrohr at 90°-130° C. and 0.005 mm Hg to give 75.50 g of ethyl β-cyano(5-methyl-2-thiophene)propaneoate as an oil.

d. β-cyano-(5-methyl-2-thiophene) propanic acid

A 74.0 g (0.33moles) sample of ethyl-β-cyano (5-methyl-2-thiophene) propaneoate, the product of Example 1c., was taken up in refluxing MeOH. A solution of 332 ml (0.33 moles) 1N sodium hydroxide was added dropwise over 40 min. The reaction was stirred for an additional 10 min. before cooling. The reaction was poured into excess 3N hydrochloric acid and ice. The mixture was extracted three times with Et$_2$O and the organics were combined, washed with water, brine and dried (MgSO$_4$). The solvent was evaporated in vacuo leaving an oil which solidified upon standing to give 59.19 g of β-cyano-(5-methyl-2-thiophene) propanoic acid, mp 85°-88° C.

e. 4H-Cyclopenta[b]thiophene-4-oxo-6-carboxylic Acid

A. 300 g sample of PPA was placed under argon in a flask and heated to 95° C. on a steam bath. 29 g (0.15 moles) β-cyano-(5-methyl-2-thiophene) propanoic acid the product of Example 1d., was added in portions. The reaction mixture was heated for 35 hr cooled and 1.5 L of water was added. The mixture was heated on a steam bath for 2 hr. The reaction mixture was cooled, and extracted with Et$_2$O four times. The organics were combined, washed with water. brine and dried (MgSO$_4$). Evaporation of the solvent in vacuo gave 10.64 g of 4H-cyclopenta[b]thiophene-4-oxo-6-carboxylic acid, mp 126°-128° C.

f. Ethyl 4H-Cyclopenta[b]thiophene-4-oxo-6-carboxylate

A 10.64 g (0.054 moles) sample of 4H-cyclopenta[b]thiophene-4-oxo-6-carboxylic acid, the product of Example 1e., was dissolved in 150 ml of absolute EtOH and 3.87 ml (0.059 moles) methanesulfonic acid was added. Heated to reflux for two hr. The reaction mixture was partitioned between Et$_2$O and sodium bicarbonate and the solid formed was filtered off. The filtrate was extracted two more times with Et$_2$O and the organics were combined, washed with water, brine and dried (MgSO$_4$). Evaporation of the solvent gave 9.03 g of ethyl 4H-cyclopenta[b]thiophene-4-oxo-6-carboxylate. mp 50°-55° C.

g. Ethyl 4H-Cyclopenta[b]thiophene-6-carboxylate

A. 17.53 g (0.078 moles) sample of ethyl 4H-cyclopenta-[b]thiopene-4-oxo-6-carboxylate, the product of Example 1f., was dissolved in 200 ml of dry THF and placed under argon. A 77.1 g sample of zinc dust was added and the suspension was cooled to −5° C. 116 ml (0.23 moles) of 2N hydrogen chloride in THF was added dropwise over 55 min. The ice bath was removed and the reaction was stirred at room temperature for two hrs. A 2N solution of hydrogen chloride in THF was added until the pH=1. After stirring for one hr. the solid was filtered off. The filtrate was evaporated in vacuo. The residue was dissolved in Et$_2$O, washed with water, sodium bicarbonate, water, brine and dried (MgSO$_4$). Evaporation of the solvent gave 23.12 g of a brown oil. Flash chromatography on silica gel using 1:40 EtOAc:hexane as the elutant gave 1.25 g of ethyl 4H-cyclopenta-[b]thiophene-6-carboxylate.

h. Ethyl 5,6-Dihydro-2-methyl-3-[4-(methylthio)benzoyl) -4H-cyclopenta[b]thiophene-6-carboxylate.

A 14.25 g (0.068 moles) sample of ethyl 4H-cyclopenta[b]thiophene-6-carboxylate, the product of Example 1g., and 13.92 g p-(methylthio)benzoyl chloride were dissolved in 410 ml of dry nitromethane and placed under argon and cooled to −20° C. An 8 ml sample of SnCl$_4$ was added dropwise controlling the temperature at −20° C. After the addition was complete the reaction mixture was stirred at −20° C. for 15 min. after which it was allowed to warm slowly to room temperature and stirred for 30 min. The reaction was poured into ice water and extracted three times with Et$_2$O. The organics were combined, washed with 3-dimethylaminopropylamine solution, 3N hydrochloric acid, water, brine, and dried (MgSO$_4$). Evaporation of the solvent gave a dark green oil which was flash chromatographed on silica gel using 1:20 EtOAc:hexane as the eluant. The resulting solid was recrystallized from methylcyclohexane/EtOAC to give 15.32 g of ethyl 5,6-dihydro-2-methyl-3-[4-(methylthio)benzoyl]-4H-cyclopenta[b]thiophene-6-carboxylate, mp 62-64° C.

i. 5,6-Dihydro-2-methyl-3-[4-(methylthio)benzoyl]-4H-cyclopenta[b]thiophene-6-carboxylic acid A 12.32 g (0.034 moles) sample of ethyl 5,6-dihydro-2-methyl-3-[4-(methyl-thio)benzoyl]-4H-cyclopenta[b]-thiophene-6-carboxylate, the product of Example 1h., was dissolved in 200 ml of refluxing MeOH. 81.32 ml (0.044 moles) of 0.5M sodium hydroxide was added dropwise over 45 min. The reaction was stirred for an additional 20 min at reflux. The MeOH was evaporated in vacuo and the residue was poured into 3N hydrochloric acid and ice. A sticky solid was filtered off, washed with water and was taken up in Et$_2$O. The ether was washed with brine and dried (MgSO$_4$). Evaporation of the solvent gave a tan solid which was recrystalized from acetonitrile to give 10.00 g of 5,6-dihydro-2-methyl-3-(4-(methylthio)benzoyl)-4H-cyclopenta[b]thiophene-6-carboxylic acid (88%), mp 131°-133° C.

EXAMPLE 2 a. Ethyl 5,6-Dihydro-2-methyl-3-[4-(methylsulfinyl) benzoyl]-4H-cyclopenta[b]-thiophene-6-carboxylate To a solution of 1.5 g (0.0042 moles) ethyl 5,6-dihydro-2-methyl-3-[4-(methylthio)benzoyl]-4H-cyclopenta[b]thiophene- 6-carboxylate, the product of Example 1h., in 40 ml of glacial acetic acid was added 0.43 ml (0.0042 moles) of 30% aqueous H$_2$O$_2$. After stirring overnight water was added and the acetic acid was evaporated in vacuo. The residue was taken up in chloroform, washed with brine and dried (MgSO$_4$). Evaporation of the solvent in vacuo gave an orange oil. Flash chromatography on silica gel with 1:3 acetone:hexane as eluant gave 1.37 g of ethyl 5,6-dihydro-2-methyl-3-[(4-(methylsulfinyl)benzoyl]-4H-cyclopenta[b]thiophene-6-carboxylate as a yellow oil.

b. 5,6-Dihydro-2-methyl-3-[(4-(methylsulfinyl)benzoyl]-4H-cyclopenta [b]thiophene-6-carboxylic acid.

To a solution of 2.29 g (0.0061 moles) ethyl 5,6-dihydro-2-methyl-3-(4-(methylsulfinyl) benzoyl)-4H-cyclopenta[b]thiophene-6-carboxylate, the product of Example 1a. in 40 ml of methanol at reflux was added 9.1 ml (0.0091 moles) of 1N sodium hydroxide dropwise. After 20 min. of refluxing the mixture was cooled in an ice bath and poured into 3N hydrogen chloridede dropwise. After 20 min. of refluxing the mixture was cooled in an ice bath and poured into 3N hydrogen chloride and ice. Solid 5,6-dihydro-2-methyl-3-[4-(methylsulfinyl) benzoyl]-4H-cyclopenta[b]thiophene-6-carboxylic acid was collected. The filtrate was extracted with chloroform, washed with brine and dried (MgSO4). Evaporation of the solvent gave solid acid which was recrystallized from acetonitrile. The two batches of solid were combined and recrystallized from acetonitrile to give 1.45 g of 5,6-dihydro-2-methyl-3-(4(methylsulfinyl)benzoyl)-4H-cyclopenta[b]thiophene-6-carboxylic acid, mp 209-213° C.

MODIFICATION A

Ethyl β-Cyano-(5-methyl-2-thienyl)propanoate

A 60 g (0.22 moles) sample of diethyl 2-[(5-methyl-2-thienyl)methylene] propanedioate, the product of Example 1a., was dissolved in 1850 ml 95% EtOH and heated to reflux. A 27 g (0.39 moles) sample of potassium cyanide in 100 ml water was added dropwise over 40 min. The reaction was stirred at reflux for 1.5 hr. After cooling the reaction was filtered and the filtrate was evaporated in vacuo. The residue was partitioned between Et2O and water. The aqueous layer was washed five times with Et2O and the organics were combined, washed with water, brine and dried (MgSO4). Evaporation in vacuo gave 20.05 g of ethyl βcyano(5-methyl-2-thienyl)propanoate.

MODIFICATION B

Ethyl 4H-Cyclopenta[b]thiophene-4-oxo-6-carboxylate

A 300 g sample of PPA was heated to 100° C. under argon. 22.04 g (0.11 moles) β-cyano-(5-methyl-2-thiophene)-propanoic acid was added portionwise and the mixture was stirred at 100° C. for 3 hr. The reaction was cooled and 750 ml of ice water was added. After stirring for 20 min. the reaction was filtered. Upon Et2O extraction a precipitate of 4H-cyclopenta[b]thiophene-4-oxo-6-carboxamide (characterized NMR and MS-m/e195) was collected. From the filtrate the Et2O was separated off and the aqueous layer was extracted three times with Et2O. The Et2O layers were combined and evaporated in vacuo to give 4H-cyclopenta[b]thiophene-4-oxo-6-carboxylic acid (characterized NMR and MS-m/e=196). The aqueous layer was made neutral by potassium carbonate addition and placed on a continuous extractor where it was extracted with chloroform overnight. Evaporation of the chloroform gave more of the amide. 3.54 g of the crude acid and 15.85 g of the crude amide were obtained. 11.96 g (0.061 moles) of the crude amide and 1.24 g (0.0063 moles) of the crude acid were taken up in 500 ml of refluxing absolute EtOH. 9.8 ml (0.14 moles) methanesulfonic acid was added over one hr. Refluxing was continued for four hr after which the EtOH was evaporated in vacuo. The residue was partitioned between Et2O and water. The aqueous layer was extracted four times with Et2O and the organics were combined, washed with sodium bicarbonate solution, water, brine and dried (MgSO4). Evaporation of the solvent in vacuo gave a dark oil. The oil was extracted four times with hexane, the extracts were combined, cooled and the solid collected. The remaining oil was flashed chromatographed on silica gel using 1:10 EtOAc:hexane as the elutant. The material from the chromatography was combined with the solid to give 9.99 g of ethyl-4H-cyclopenta[b]-thiophene-4-oxo-6-carboxylate, mp 62°-64° C.

What is claimed is:

1. A cyclopentathiophene of the following formula (I) or (II)

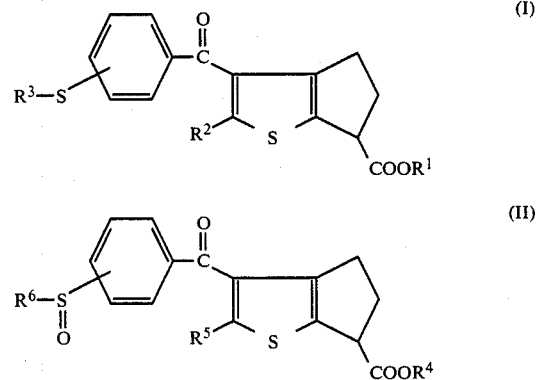

wherein
R¹ and R⁴ are hydrogen or alkyl;
R² and R⁵ are alkyl; and
R³ and R⁶ are alkyl,
and the pharmaceutically acceptable base-addition salts thereof where R¹ or R⁴ is hydrogen.

2. The cyclopentathiophene of claim 1, wherein said cyclopentathiophene is of the formula (I).

3. The cyclopentathiophene of claim 1, wherein said cyclopentathiophene is of the formula (II).

4. The cyclopentathiophene of claim 1, wherein said alkyl for R¹, R⁴, R², R⁵, R³, and R⁶ is alkyl of about 1 to 6 carbons.

5. The cyclopentathiophene of claim 1, wherein said R³ S- and R⁶ SO- moieties in formulae (I) and (II), respectively, are at the para position.

6. The cyclopentathiophene of claim 1, wherein said R³ S- and R⁶ SO- moieties in formulae (I) and (II), respectively, are at the meta position.

7. The cyclopentathiophene of claim 1, wherein said R³ S- and R⁶ SO- moieties in formulae (I) and (II), respectively, are at the ortho position.

8. The cyclopentathiophene of claim 1, wherein said R² and R⁵ are methyl.

9. The cyclopentathiophene of claim 1, wherein said R³ and R⁶ are methyl.

10. The cyclopentathiophene of claim 1, wherein said cyclopentathiophene is 5,6-dihydro-2-methyl-3-(4-(methylthio)benzoyl)-4H-cyclopenta [b]thiophene-6-carboxylic acid, or 5,6-dihydro-2-methyl-3-[4-(methylsulfinyl)benzoyl]-4H-cyclopenta[b]thiophene-6-carboxylic acid, or a pharmaceutically acceptable base-addition salt thereof.

11. A pharmaceutical composition for the treatment of inflammation in a mammal which comprises an anti-inflammatory amount of a cyclopentathiophene of claim 1 in association with a pharmaceutically acceptable carrier.

12. A method for the treatment of inflammation in a mammal which comprises administering to the mammal, the composition of claim 11.

13. The method of claim 12, wherein said administration is topical.

14. A pharmaceutical composition for the treatment of arthritis in a mammal which comprises an anti-inflammatory amount of a cyclopentathiophene of claim 1 in association with a pharmaceutically acceptable carrier.

15. A method for the treatment of arthritis in a mammal which comprises administering to the mammal the composition of claim 14.

* * * * *